US005808138A

United States Patent [19]
Laqua et al.

[11] Patent Number: 5,808,138
[45] Date of Patent: Sep. 15, 1998

[54] STABLE POLYISOCYANATE COPOSITIONS OBTAINABLE BY PHOSGENE-FREE METHODS AND THEIR PREPARATION

[75] Inventors: Gerhard Laqua, Mannheim; Bernd Bruchmann, Ludwigshafen; Stefan Wolff, Limburgerhof, all of Germany

[73] Assignee: BASF Aktiengesellschaft, Ludwigshafen, Germany

[21] Appl. No.: 563,883

[22] Filed: Nov. 21, 1995

Related U.S. Application Data

[63] Continuation of Ser. No. 283,428, Aug. 1, 1994, abandoned.

[51] Int. Cl.$^6$ .................................................. C07C 7/20
[52] U.S. Cl. ............................................. 560/331
[58] Field of Search .............................. 560/331; 252/397, 252/399, 373

[56] References Cited

U.S. PATENT DOCUMENTS

| | | | |
|---|---|---|---|
| 3,247,236 | 4/1966 | Adams | 560/331 |
| 3,247,237 | 4/1966 | Hagemeyer, Jr. | |
| 3,330,847 | 7/1967 | Cross | 560/331 |
| 4,638,016 | 1/1987 | Arai et al. | 528/53 |
| 4,828,753 | 5/1989 | Robin | |
| 5,087,739 | 2/1992 | Bohmholdt et al. | 560/345 |
| 5,144,031 | 9/1992 | Pedain | 544/193 |
| 5,175,349 | 12/1992 | Gupta et al. | |
| 5,189,205 | 2/1993 | McGhee et al. | 560/345 |
| 5,258,548 | 11/1993 | Imokawa | |
| 5,288,865 | 2/1994 | Gupta | 544/200 |
| 5,298,651 | 3/1994 | McGhee et al. | 560/345 |
| 5,349,081 | 9/1994 | McGhee | 560/345 |
| 5,451,697 | 9/1995 | McGhee et al. | 560/345 |

OTHER PUBLICATIONS

EPO Search Report dated Dec. 27, 1994; Translation of EPO Search Report.

*Primary Examiner*—Jeffrey C. Mullis
*Attorney, Agent, or Firm*—Fernando A. Borrego

[57] ABSTRACT

Stable (cyclo)aliphatic polyisocyanate compositions obtainable by phosgene-free methods, preferably by thermal cleavage of (cyclo)aliphatic polycarbamates, are stabilized with carbon dioxide, advantageously in an amount of up to 0.3% by weight.

4 Claims, No Drawings

STABLE POLYISOCYANATE COPOSITIONS OBTAINABLE BY PHOSGENE-FREE METHODS AND THEIR PREPARATION

This is a continuation of application Ser. No. 08/283,428 filed Aug. 1, 1994 now abandoned.

(Cyclo)aliphatic polyisocyanate compositions obtainable by phosgene-free methods, preferably by thermal cleavage of (cyclo)aliphatic polycarbamates, are stabilized by the addition of carbon dioxide.

Organic polyisocyanates, for example aromatic, cycloaliphatic and aliphatic di- and polyfunctional polyisocyanates, can be prepared by various processes (Annalen der Chemie 562 (1949), 75 et seq.), The preparation of organic polyisocyanates by phosgenation of organic polyamines to give the corresponding polycarbamoyl chlorides and the thermal cleavage thereof into organic polyisocyanates and hydrogen chloride have proven particularly useful in industry, so that at present only this production process is used industrially.

Problems in this procedure are the high conversion of chlorine via phosgene and carbamoyl chloride into hydrogen chloride, the toxicity of the phosgene and the associated expensive safety measures, the corrosiveness of the reaction mixture, the instability of the solvents usually used and the formation of chlorine-containing and chlorine-free byproducts which play a decisive role in determining the physical properties, for example the color, the viscosity and the vapor pressure, and the chemical properties, such as reactivity, shelf-life, etc., of the polyisocyanates and the mechanical properties of the polyisocyanate polyadducts prepared from such polyisocyanates.

There has therefore been no lack of attempts to prepare organic, preferably aromatic polyisocyanates without the use of phosgene, ie. by phosgene-free methods.

According to EP-B-0 126 299 (US-A-4 596 678), EP-B-0 126 300 (US-A-4 596 679) and EP-A-0 355 443 (US-A-5 087 739), (cyclo)aliphatic diisocyanates, such as hexamethylene 1,6-diisocyanate (HDI), and/or isomeric aliphatic diisocyanates where the alkylene radical is of 6 carbon atoms and 1-isocyanato-3-isocyanatomethyl-3,5,5-trimethylcyclohexane (isophorone diisocyanate or IPDI) can be prepared by the circulation method, by reacting the (cyclo)aliphatic diamines with urea and alcohols and, if required, N-unsubstituted carbamates, dialkyl carbonates and other byproducts recycled from the reaction process to give (cyclo)aliphatic biscarbamates and subjecting the latter to thermal cleavage to give the corresponding diisocyanates and alcohols.

Depending on the type of preparation process, the organic polyisocyanates contain different byproducts, many of which have an unknown structure, the chlorine-containing byproducts in particular influencing the shelf-life, reactivity and color of the composition.

According to US-A-3 330 849, for example, organic polyisocyanates can be stabilized to discoloration and precipitation by adding sulfonyl isocyanates. As a result of the addition of metal naphthenates, for example cadmium, cobalt, copper, lead, manganese or zinc naphthenate, the hydrolyzable chlorine content of isocyanates can be reduced according to US-A-3 373 182. US-A-3 384 653 and US-A-3 449 256 describe the improvement of the shelf-life of 4,4'-diphenylmethane diisocyanate by a treatment at from 160° to 250° C. with trialkyl phosphates. According to US-A-3 458 558, the content of hydrolyzable chlorine compounds in organic isocyanates can also be reduced with copper, silver, nickel, iron and zinc at above 100° C. According to US-A-3 479 393, trialkylaminoboranes stabilize isocyanates to discoloration. According to US-A-3 535 359, orthocarbonic esters are suitable for stabilizing organic isocyanates to an increasing viscosity. According to US-A-3 585 229, polyisocyanate mixtures containing diphenylmethane diisocyanate can be decolorized by adding diphenyl decyl phosphite. According to US-A-3 692 813, organic polyisocyanates can be stabilized to decomposition with the aid of oxycarbonyl isocyanates having at least one group of the formula —O—CO—NCO. According to US-A-3 715 381, 2,6-di-tert-butyl-p-cresol may be used for stabilizing organic polyisocyanates to discoloration. According to US-A-3 970 680, diphenylmethane diisocyanates may also be stabilized by adding tertiary amines. According to US-A-4 065 362, organic isocyanates may be purified by treating them at above 100° C. with a metal salt of mercaptobenzothiazole, a metal salt of alkyl-substituted dithiocarbamic acid, an alkyl-substituted phenol, a thiobisphenol or a triaryl phosphite. According to US-A-3 247 236, diisocyanates prepared by reacting diamines with phosgene and purified by distillation can be stabilized by adding carbon dioxide or sulfur dioxide. The disadvantages of this process are the good solubility of the sulfur dioxide in the polyisocyanate and the occurrence of discoloration during storage. Another disadvantage is that the polyisocyanates stabilized with carbon dioxide can undergo trimerization reactions only after considerable difficulties have been overcome. For the trimerization of hexamethylene diisocyanate, according to DE-A-3 806 276 the latter must be freed from carbon dioxide down to a residual content of less than 20 ppm. US-A-3 247 236 and the other abovementioned patent publications do not describe the stabilization of organic polyisocyanates prepared by phosgene-free methods.

(Cyclo)aliphatic polyisocyanates obtainable by phosgene-free methods, in particular by thermal cleavage of (cyclo)aliphatic polycarbamates, do not have a long shelf-life. Their instability is due to the lack of hydrolyzable chlorine compounds and to the presence of catalytic impurities of unknown structure which, for example, promote the formation of oligomers. At low temperatures, for example at +5° C. or lower, for example, hexamethylene diisocyanate (HDI) tends to form linear HDI oligomers of the formula

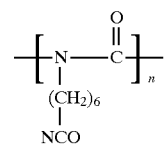

The increase in molecular weight associated with an increase in viscosity may lead to gelling of the polyisocyanate, for example of the HDI. Such products are difficult to handle, can no longer be reproducibly converted into polyisocyanate polyadducts and must therefore be discarded. At higher storage temperatures, for example, the reactivity of the HDI prepared by phosgene-free methods greatly decreases, in particular in the trimerization reaction catalyzed with quaternary ammonium hydroxide compounds. Intensely colored, isocyanurate-containing polyisocyanates which in particular can no longer be used as coating raw materials are obtained.

It is an object of the present invention to stabilize (cyclo)aliphatic polyisocyanates prepared by phosgene-free methods by suitable measures without adversely affecting the reactivity of the polyisocyanates. The oligomerization of the polyisocyanates and an increase in viscosity of the polyisocyanate composition, as well as their discoloration during storage, should likewise be prevented.

We have found, surprisingly, that this object is achieved using carbon dioxide as a stabilizer.

The present invention therefore relates to stable (cyclo) aliphatic polyisocyanate compositions which contain i) a (cyclo)aliphatic polyisocyanate prepared by a phosgene-free method, preferably by thermal cleavage of (cyclo)aliphatic polycarbamates, and ii) carbon dioxide.

As a result of the addition of carbon dioxide, it was possible, surprisingly, to stabilize the reactivity of the (cyclo)aliphatic polyisocyanates and their color number over a storage time of at least 12 weeks at room temperature. The trouble-free trimerization of the (cyclo)aliphatic polyisocyanates with a quaternary ammonium compound, such as N,N,N-trimethyl-N-(2-hydroxypropyl)-ammonium 2-ethylhexanoate, as a trimerization catalyst was also surprising and unforeseeable. In contrast to DE-A-38 06 276, in which isocyanurate-containing polyisocyanates having high color numbers are obtained in the presence of high carbon dioxide contents from monomeric polyisocyanates prepared by phosgenation, in the trimerization of the novel (cyclo) aliphatic polyisocyanate compositions the color number is further reduced and thus additionally improved.

The novel polyisocyanate compositions may contain any (cyclo)aliphatic polyisocyanates, with the proviso that they have been prepared by suitable processes in the absence of phosgene. (Cyclo)aliphatic polyisocyanates which are obtainable by thermal cleavage of (cyclo)aliphatic polycarbamates have proven very suitable and are therefore preferably used. Useful aliphatic polyisocyanates advantageously have from 3 to 16, preferably from 4 to 12, carbon atoms in the linear or branched alkylene radical, and suitable cycloaliphatic polyisocyanates advantageously have from 4 to 18, preferably from 6 to 15, carbon atoms in the cycloalkylene radical. Examples are 1,4-diisocyanatobutane, 2-ethyl-1,4-diisocyanatobutane, 1,5-diisocyanatopentane, 2-methyl-1,5-diisocyanatopentane, 2,2-dimethyl-1,5-diisocyanatopentane, 2-ethyl-2-propyl-1,5-diisocyanatopentane, 2-ethyl-2-butyl-1,5-diisocyanatopentane, 2-alkoxymethylene-1,5-diisocyanatopentane, hexamethylene 1,6-diisocyanate, 2,4,4- and 2,2,4-trimethylhexamethylene 1,6-diisocyanate, 1,7-diisocyanatoheptane, 1,8-diisocyanatooctane, 1,10-diisocyanatodecane, 1,12-diisocyanatododecane, 4,4'-diisocyanatodicyclohexylmethane, 2,4'-diisocyanatodicyclohexylmethane and mixtures of the diisocyanatodicyclohexylmethane isomers, 1,3-diisocyanatocyclohexane and isomer mixtures of diisocyanatocyclohexanes and 1-isocyanato-3-isocyanatomethyl-3,5,5-trimethylcyclohexane. Preferably used (cyclo)aliphatic polyisocyanates are hexamethylene 1,6-diisocyanate, isomeric aliphatic diisocyanates where the alkylene radical is of 6 carbon atoms and mixtures thereof and 1-isocyanato-3-isocyanatomethyl-3,5,5-trimethylcyclohexane.

As stated above, the (cyclo)aliphatic diisocyanates are preferably prepared by thermal cleavage of the corresponding dicarbamates. This cleavage may be carried out, for example, at from 150° to 300° C., preferably from 180° to 250° C., and from 0.001 to 2 bar, preferably from 1 to 200 mbar, in the absence or, preferably, in the presence of catalysts in suitable cleavage reactors, such as thin-film evaporators or preferably heating-element evaporators according to EP-A-0 524 554. The diisocyanates and alcohols formed in the cleavage can be separated, for example by fractional condensation or preferably by rectification, and the diisocyanates can be additionally purified, for example by distillation.

For the stabilization of the (cyclo)aliphatic polyisocyanates obtainable by phosgene free methods, preferably by thermal cleavage of (cyclo)aliphatic polycarbamates, the carbon dioxide may be used in amounts up to the saturation point of the carbon dioxide in the specific polyisocyanate, without as a result adversely affecting its physical or chemical properties, in particular its ability to undergo partial or complete trimerization. For economic reasons, the carbon dioxide is advantageously used in an amount of up to 0.3, preferably from 0.004 to 0.3, in particular from 0.05 to 0.15, % by weight, based on the total weight of the polyisocyanate composition.

The carbon dioxide may be introduced, for example, in powder form, advantageously with stirring, into the (cyclo) aliphatic polyisocyanates prepared by phosgene-free methods. In another process variant, carbon dioxide may be forced in the required amount into the (cyclo)aliphatic polyisocyanate under pressure and advantageously with stirring. In a preferred embodiment, the gaseous carbon dioxide is allowed to bubble in the required amount through the (cyclo)aliphatic polyisocyanate, and carbon dioxide may be additionally introduced during the storage time. The carbon dioxide is advantageously introduced into the storage containers via suitable nozzles.

(Cyclo)aliphatic polyisocyanate compositions stabilized by the novel process, preferably the hexamethylene 1,6-diisocyanate and 1-isocyanato-3-isocyanatomethyl-3,5,5-trimethylcyclohexane compositions The (cyclo)aliphatic polyisocyanate compositions obtainable by phosgene-free methods, preferably by thermal cleavage of (cyclo)aliphatic polycarbamates, can be stabilized by adding carbon dioxide alone. However, it is also possible to use the carbon dioxide in combination with other compounds having a stabilizing effect.

Examples of suitable additional stabilizers are phenolic antioxidants, so that these are preferably concomitantly used. For example, phosphorus-containing stabilizers may also be present.

Examples of suitable phenolic antioxidants are compounds which have at least one sterically hindered phenolic group. Examples of such antioxidants are: 2,6-di-tert-butyl-4-methylphenol, 2,4,6-tri-tert-butylphenol, 2,2'-methylenebis-(4-methyl-6-tert-butylphenol), 2,2'-thiobis-(4-methyl-6-tert-butylphenol), 4,4'-thiobis-(3-methyl-6-tert-butylphenol), 4,4'-butylidenebis-(6-tert-butyl-3-methylphenol), 4,4'-methylidenebis-(2,6-di-tert-butylphenol), 2,2'-methylenebis-[4-methyl-6-(1-methylcyclohexyl)-phenol], tetrakis[methylene-3-(3,5-di-tert-butyl-4-hydroxyphenyl)-propionyl]-methane, 1,3,5-trimethyl-2,4,6-tris-(3,5-di-tert-butyl-4-hydroxybenzyl)-benzene, N,N'-hexamethylenebis-(3,5-di-tert-butyl-4-hydroxyhydrocinnamide), octadecyl 3-(3,5-di-tert-butyl-4-hydroxyphenyl)-propionate, 1,3,5-tris-(3,5-di-tert-butyl-4-hydroxybenzyl) isocyanurate, 1,1,3-tris-(5-tert-butyl-4-hydroxy-2-methylphenyl)-butane, 1,3,5-tris-(3,5-di-tert-butyl-4-hydroxybenzyl)-mesitylene, ethylene glycol bis-[3,3-bis-(3'-tert-butyl-4'-hydroxyphenyl)-butyrate], 2,2'-thiodiethyl bis-3-(3,5-di-tert-butyl-4-hydroxyphenyl)-propionate, di-(3-tert-butyl-4'-hydroxy-5-methylphenyl)-dicyclopentadiene, 2,2'-methylenebis-(4-methyl-6-cyclohexylphenol), 1,6-hexanediol bis-(3,5-di-tert-butyl-4-hydroxyphenyl)-propionate, 2,4-bis-(n-octylthio)-6-(4-hydroxy-3,5-di-tert-butylanilino)-1,3,5-triazine, diethyl 3,5-di-tert-butyl-4-hydroxybenzylphosphonate and triethylene glycol bis-3-(tert-butyl-4-hydroxy-5-methylphenyl)-propionate.

For example, octadecyl 3-(3,5-di-tert-butyl-4-hydroxyphenyl)-propionate, 2,2'-methylenebis-(4-methyl-6- cyclohexylphenol), 2,2'-methylenebis-(4-methyl-6-tert-butylphenol), triethylene glycol bis-3-(tert-butyl-4-hydroxy-5-methylphenyl)-propionate, tetrakis-[methylene-3-(3,5-di-tert-butyl-4-hydroxyphenyl)-propionyl]-methane and in particular 2,6-di-tert-butyl-4-methylphenol have proven very suitable and are therefore preferably used.

Examples of suitable phosphorus-containing stabilizers are distearyl pentaerythrityl diphosphite, tris-(nonylphenyl) phosphite, tetrakis-(2,4-di-tert-butylphenyl-4,4'-biphenylene) diphosphonite, tris-(2,4-di-tert-butylphenyl) phosphite, neopentylglycol triethylene glycol diphosphite, diisodecyl pentaerythrityl diphosphite, tristearyl phosphite, trilauryl phosphite and triphenyl phosphite.

The additional stabilizers, preferably the phenolic antioxidants and/or phosphorus-containing compounds mentioned by way of example, may be used, for example, in amounts of from 0.001 to 0.1, preferably from 0.005 to 0.05, % by weight, based on the weight of the polyisocyanate composition.

The (cyclo)aliphatic polyisocyanates prepared in the absence of phosgene and preferably obtainable by thermal cleavage of polycarbamates are thus preferably stabilized by a combination of carbon dioxide, phenolic antioxidants and/or phosphorus-containing compounds and contain advantageously up to 0.3, preferably from 0.004 to 0.3, in particular from 0.05 to 0.15, % by weight of carbon dioxide, from 0 to 0.1, preferably from 0.001 to 0.05, in particular from 0.01 to 0.03, % by weight of at least one phenolic antioxidant and from 0 to 0.1, preferably from 0.001 to 0.05, in particular from 0.01 to 0.03, % by weight of at least one phosphorus-containing compound, the percentages being based on the total weight.

EXAMPLES

Example 1

A hexamethylene 1,6-diisocyanate (HDI) composition prepared by thermal cleavage of 1,6-hexamethylenedibutylurethane was gassed with dry carbon dioxide at 23° C. for 5 minutes. The HDI sample, which had a carbon dioxide content of about 1000 ppm, was stored in a V2A stainless steel container at 40° C.

Comparative Example I

Some of the abovementioned HDI composition was stored under the same conditions but in the absence of carbon dioxide.

Preparation of isocyanurate-containing polyisocyanate mixtures:

After a storage time of 30 days, the HDI compositions mentioned above were trimerized in the presence of 500 ppm of N,N,N-trimethyl-N-(2-hydroxypropyl)-ammonium 2-ethylhexanoate at 80° C. while stirring. After one hour, the reaction was stopped by adding dibutyl phosphate.

The following properties of the reaction mixtures were measured:

|  | Example 1 | Comparative Example I |
| --- | --- | --- |
| HDI content after storage [% by wt.] | >99.9 | 99.62 |
| Remaining components to 100% by weight: | oligomers | oligomers |
| NCO content of the reaction mixture after the trimerization [% by wt.] | 39.3 | 47.8 |
| Hazen color number of the reaction mixture after the trimerization | 169 | 412 |

The results show that, after storage under carbon dioxide, the novel HDI composition according to Example 1 had a lower oligomer content, ie. is more stable, and the reaction mixture after the trimerization had a lower color number, ie. a paler color, than the HDI composition according to Comparative Example I.

Example 2

An HDI composition prepared by thermal decomposition of 1,6-hexamethylenedibutylurethane was gassed with dry carbon dioxide at 23° C. for 5 minutes, after which 100 mol ppm of 2,6-di-tert-butyl-4-methylphenol were added. The HDI composition, which had a carbon dioxide content of about 1000 ppm, was stored in a V2A stainless steel container at 40° C.

Comparative Example II

Some of the abovementioned HDI composition was stabilized only with 100 mol ppm of 2,6-di-tert-butyl-4-methylphenol and was stored similarly to Example 2.

Preparation of isocyanurate-containing polyisocyanate mixtures

After a storage time of 30 days, the HDI compositions according to Example 2 and Comparative Example II were trimerized in the presence of 500 ppm of N,N,N-trimethyl-N-(2-hydroxypropyl)-ammonium 2-ethylhexanoate at 80° C. while stirring. After one hour, the reaction was stopped by adding dibutyl phosphate.

The following results were determined for the reaction mixtures:

|  | Example 2 | Comparative Example II |
| --- | --- | --- |
| HDI content after storage [% by wt.] | 99.67 | 98.75 |
| Remaining components to 100% by weight: | oligomers | oligomers |
| NCO content of the reaction mixture after the trimerization [% by wt.] | 39.7 | 39.4 |
| Hazen color number of the reaction mixture after the trimerization | 78 | 145 |

Example 2 shows that the color number of isocyanurate-containing polyisocyanates of HDI compositions stabilized with carbon dioxide was further improved by the presence of 2,6-di-tert-butyl-4-methylphenol as an additional stabilizer.

Example 3

An HDI composition prepared by thermal decomposition of 1,6-hexamethylenedibutylurethane was gassed with dry carbon dioxide at 23° C. for 5 minutes, after which 50 mol ppm of 2,6-di-tert-butyl-4-methylphenol and 50 mol ppm of triphenyl phosphite were added. The HDI composition, which had a carbon dioxide content of about 1000 ppm, was stored in a V2A stainless steel container at 5° C.

Comparative Example III

Some of the abovementioned HDI composition was stabilized only with 50 mol ppm of 2,6-di-tert-butyl-4-methylphenol and 50 mol ppm of triphenyl phosphite and was stored similarly to Example 3.

Preparation of isocyanurate-containing polyisocyanate mixtures

After a storage time of 30 days, the HDI compositions according to Example 3 and Comparative Example III were trimerized in the presence of 500 ppm of N,N,N-trimethyl-N-(2-hydroxypropyl)-ammonium 2-ethylhexanoate at 80° C. while stirring. After one hour, the reaction was stopped by adding dibutyl phosphate.

The following results were determined for the reaction mixtures:

|  | Example 3 | Comparative Example III |
|---|---|---|
| HDI content after storage [% by wt.] | >99.9 | 99.69 |
| Remaining components to 100% by weight: | oligomers | oligomers |
| NCO content of the reaction mixture after the trimerization [% by wt.] | 38.3 | 38 |
| Hazen color number of the reaction mixture after the trimerization | 49 | 58 |

Example 3 shows that the color number of isocyanurate-containing polyisocyanates of HDI compositions stabilized with carbon dioxide was further improved by the presence of 2,6-di-tert-butyl-4-methylphenol and triphenyl phosphite as additional stabilizers.

We claim:

1. A process for improving the shelf-life of aliphatic or cycloaliphatic polyisocyanate compositions prepared by a phosgene-free method and lacking hydrolyzable chlorine compounds, wherein carbon dioxide is added to an already prepared polyisocyanate composition by bubbling gaseous carbon dioxide or by adding solid carbon dioxide in an amount of from 0.004 to 0.3% by weight, based on the total weight.

2. A process for improving the shelf-life of aliphatic or cycloaliphatic polyisocyanate compositions prepared by thermal cleavage of aliphatic or cycloaliphatic polycarbamates and lacking hydrolyzable chlorine compounds, wherein carbon dioxide is added to an already prepared polyisocyanate composition by bubbling gaseous carbon dioxide or by adding solid carbon dioxide in an amount of from 0.004 to 0.3% by weight, based on the total weight.

3. A process as claimed in claim 2, wherein the polyisocyanate composition comprises the aliphatic polyisocyanate comprising hexamethylene 1,6-diisocyanate.

4. A process as claimed in claim 2, wherein the polyisocyanate composition comprises the cycloaliphatic polyisocyanate comprising 1-isocyanato-3-isocyanatomethyl-3,5,5-trimethylcyclohexane.

* * * * *